US007646002B2

(12) United States Patent
Sendai

(10) Patent No.: US 7,646,002 B2
(45) Date of Patent: Jan. 12, 2010

(54) FLUORESCENCE DETECTING SYSTEM

(75) Inventor: Tomonari Sendai, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 338 days.

(21) Appl. No.: 11/386,801

(22) Filed: Mar. 23, 2006

(65) Prior Publication Data
US 2006/0247535 A1 Nov. 2, 2006

(30) Foreign Application Priority Data
Mar. 23, 2005 (JP) ............................. 2005-083430

(51) Int. Cl.
G01N 21/64 (2006.01)
(52) U.S. Cl. .............. 250/461.2; 250/458.1; 250/459.1; 250/461.1
(58) Field of Classification Search ............. 250/458.1, 250/459.1, 461.1, 461.2, 361 R, 372, 362
See application file for complete search history.

(56) References Cited

U.S. PATENT DOCUMENTS

| 5,324,940 | A | * | 6/1994 | Ekstrom ..................... 250/302 |
| 5,612,540 | A | * | 3/1997 | Richards-Kortum et al. ...... 250/461.2 |
| 5,833,617 | A | | 11/1998 | Hayashi |
| 5,936,731 | A | * | 8/1999 | Cabib et al. ................ 356/456 |
| 7,282,723 | B2 | * | 10/2007 | Schomacker et al. ..... 250/458.1 |
| 7,309,867 | B2 | * | 12/2007 | Costa et al. ............. 250/458.1 |
| 2004/0186351 | A1 | | 9/2004 | Imaizumi et al. |
| 2004/0197771 | A1 | * | 10/2004 | Powers et al. .................. 435/5 |
| 2004/0245350 | A1 | * | 12/2004 | Zeng .......................... 236/43 |

FOREIGN PATENT DOCUMENTS

| JP | 9-308604 A | 12/1997 |
| JP | 2002-172082 A | 6/2002 |
| WO | WO 2004/106896 A2 | 12/2004 |

OTHER PUBLICATIONS

Gu Y., Qian Z., Chen J., Blessington D., Ramanujam N., Chance B.; High-Resolution Three-Dimensional Scanning Optical Image System for Intrinsic and Extrinsic Contrast Agents in Tissue; Jan. 2002; Review of Scientific Instruments; vol. 73; No. 1; pp. 172-178.*

(Continued)

Primary Examiner—David P Porta
Assistant Examiner—David S Baker
(74) Attorney, Agent, or Firm—Sughrue Mion, PLLC

(57) ABSTRACT

A fluorescence detecting system includes a stimulating light projector which projects onto an object part which has been dosed with a fluorescence agent first stimulating light in the exciting wavelength range of the fluorescence agent and second stimulating light which differs from the first stimulating light in the wavelength band and is in the exciting wavelength range of the auto-fluorescence material contained in the object part, and a fluorescence information obtainer which obtains the fluorescence from the fluorescence agent information based on the fluorescence from the fluorescence agent emitted from the object part in response to projection of the first stimulating light and the auto-fluorescence information based on the auto-fluorescence emitted from the object part in response to projection of the second stimulating light. The fluorescence agent is a fluorescence agent which does not emit fluorescence in response to projection of the second stimulating light.

13 Claims, 6 Drawing Sheets

OTHER PUBLICATIONS

European Search Report dated Jul. 18, 2007.
Gu Y. et al. "High-Resolution Three-Dimensional Scanning Optical Image System for Intrinsic and Extrinsic Contrast Agents in Tissue," Review of Scientific Instruments, AIP, Melville, NY, vol. 73, No. 1, Jan. 2002, pp. 172-178.

"New Living Body Measurement Using Light-Invitation to Medical Optics—No. 8," M. Tamura, O plus E, vol. 20, No. 7, pp. 836-840, 1998.

* cited by examiner

FLUORESCENCE DETECTING SYSTEM

BACKGROUND OF THE INVENTION

1. Field of the Invention

This invention relates to a fluorescence detecting system which detects fluorescence from the fluorescence agent information based on fluorescence from the fluorescence agent and/or auto-fluorescence information based on auto-fluorescence emitted from an object part upon projection of stimulating light onto an object part which has been dosed with a fluorescence agent in advance.

2. Description of the Related Art

There has been known a fluorescence detecting system which detects fluorescence emitted from an object part to use it for diagnosis of the tissue properties of the object part. For example, an fluorescence from the fluorescence agent detecting system is a system wherein tumor-affinity agent (e.g., ATX-S10, 5-ALA, NPe6, HAT-D01, Photofrin-2 or the like) which emits fluorescence upon excitation by light was dosed to an object in advance as a fluorescent agent to be absorbed by a part of tumor such as cancer, stimulating light in the exciting wavelength range of the agent is projected onto the part, fluorescence emitted from the agent (referred to as "fluorescence from the fluorescence agent", hereinbelow) accumulated in the part of tumor is detected, and fluorescence from the fluorescence agent information reflecting the tissue properties of the object part is obtained from the fluorescence from the fluorescence agent and displayed. Or the localization and/or the infiltration of the part of tumor are determined by comparison and analysis of the fluorescence from the fluorescence agent information, and the result of determination is displayed.

Further, there has been known a fact that the intensity and the spectrum of the fluorescence emitted from the auto-fluorescence material in an object part (referred to as "auto-fluorescence", hereinbelow) upon projection of stimulating light in a predetermined wavelength band onto the object part differs depending on whether the object part is of normal tissue or diseased tissue as shown in FIG. 9. There has been proposed an auto-fluorescence detecting system where, on the basis of this phenomenon, stimulating light in a predetermined wavelength band projected onto the object part and auto-fluorescence information reflecting the tissue properties of the object part is obtained from the auto-fluorescence and displayed or the localization and/or the infiltration of the part of tumor are determined by analysis of the auto-fluorescence information, and the result of determination is displayed. (For example, Japanese Unexamined Patent Publication No. 2002-172082)

The fluorescence detecting system of this type is generally incorporated in an endoscope, a colposcope or a microscope for surgery which are inserted into a body cavity. As a method of detecting the fluorescence, there have been known a method in which the fluorescence is two-dimensionally detected by the use of an image pick-up element such as a CCD and a method in which a fluorescence spectrum is obtained from a point on the object part by the use of a fiber and/or a spectroscope.

Further, there have been proposed various comparing/analyzing method in these fluorescence detecting systems in order for the observer to more accurately obtain information on tissue properties on the basis of fluorescence information.

When the stimulating light is projected onto an object part such as an organic tissue to image the intensity of fluorescence emitted from the object part as a fluorescence image and the fluorescence information obtained on the basis of the fluorescence image is displayed, the intensity of the stimulating light to be projected is not uniform due to the irregularities on the object part. When an auto-fluorescence image is to be taken, though the intensity of fluorescence emitted from a normal object part is substantially proportional to the illuminance of the stimulating light, the illuminance of the stimulating light is reduced in inverse proportion to square of the distance. Accordingly, the fluorescence received from a diseased tissue nearer to the light source is sometimes stronger than the fluorescence received from a normal tissue far away from the light source, which makes it infeasible to accurately determine the tissue properties of the object part only on the basis of information on the intensity of fluorescence.

In order to suppress such a problem, there has been proposed a method in which light different from the stimulating light in the wavelength band is projected onto the object part as reference light to detect the intensity of the reflecting light reflected at the object part illuminated by the reference light, and a fluorescence image based on the result of the division between the intensity of the fluorescence and the intensity of the reflecting light of the reference light is generated, that is, fluorescence information based on the difference of the light intensity of the fluorescence reflecting the tissue properties is obtained and displayed.

Further, in the case of the auto-fluorescence, since the fluorescence emitted from a normal object part and the fluorescence emitted from a diseased object part differ from each other in the shape of spectrum, there has been proposed a method in which an intensity ratio of two kinds of fluorescence obtained from different wavelength bands, e.g. a narrow band near 480 nm and a broad band from near 430 nm to near 730 nm is obtained by division and a fluorescence image based on the result of the division is displayed, that is, fluorescence information based on the difference of the shape of the spectrum of the fluorescence reflecting the organic tissue properties is obtained and displayed.

Further, this applicant has proposed a system in which stimulating light is projected onto an object part which has been dosed with a fluorescence agent to obtain the fluorescence from the fluorescence agent and the auto-fluorescence, and fluorescence information based on the fluorescence from the fluorescence agent and the auto-fluorescence is obtained. (Japanese Unexamined Patent Publication No. 9(1997)-308604)

Further, in "O plus E vol. 20, No. 7, pp. 836 to 840 (1998/7)", it has been reported that the fluorescence emitted from the object organic body is differently absorbed and scattered in the organic body depending on the wavelength band as a result of detecting and analyzing the fluorescence emitted from the organic body point to point. It has been further reported that a distribution is generated in the incident angle of the stimulating light to the surface of an organic body due to irregularity on the surface of the object and the degree of absorption or scatter changes, and the intensity of fluorescence obtained changes depending on the distance between the measuring system and the object. These influences distort the spectrum of the fluorescence obtained by the detector from the spectrum of the fluorescence originally emitted from the object.

In the technology disclosed in the above "O plus E vol. 20, No. 7, pp. 836 to 840 (1998/7)", a spectrum of light reflected at the surface of an organic body is detected and the distortion of the spectrum of fluorescence is corrected by the use of the spectrum of the reflected light. Further, this applicant has proposed a method in which reflected light the same in the wavelength band as the fluorescence to be obtained is obtained and fluorescence information where the distortion of the spectrum of fluorescence is corrected is obtained by the use of the reflected light.

Recently, technology of detecting fluorescence is improved and even very weak fluorescence becomes able to be detected. As a result, it has been found that the fluorescence from the fluorescence agent information obtained on the basis of the fluorescence from the fluorescence agent includes highly accurate information on the localization and/or the infiltration of the part of tumor and the auto-fluorescence information obtained on the basis of the auto-fluorescence includes slightly less accurate information on the localization and/or the infiltration of the part of tumor. That is, it can be said that there is a slight deviation between the auto-fluorescence information obtained on the basis of the auto-fluorescence and the fluorescence from the fluorescence agent information obtained on the basis of the fluorescence from the fluorescence agent. Accordingly, it is preferred that both the fluorescence from the fluorescence agent information and the auto-fluorescence information be obtained in order to know the tissue properties more accurately.

In Japanese Unexamined Patent Publication No. 9(1997)-308604 described above, stimulating light is projected onto the object part which has been dosed with a fluorescence agent and the fluorescence from the fluorescence agent and the auto-fluorescence are obtained. However, since the fluorescence from the fluorescence agent wavelength band and the auto-fluorescence wavelength band mingle with each other, it is impossible to discretely obtain the auto-fluorescence information based on the auto-fluorescence and the fluorescence from the fluorescence agent information based on the fluorescence from the fluorescence agent.

Though it is possible to discretely obtain the auto-fluorescence information and the fluorescence from the fluorescence agent information by obtaining the auto-fluorescence before the object part is dosed with a fluorescence agent and obtaining the fluorescence from the fluorescence agent after the object part is dosed with a fluorescence agent, this is disadvantageous in that load on the examinee is increased, for instance, the examination is elongated, and identification of the object part becomes difficult.

SUMMARY OF THE INVENTION

In view of the foregoing observations and description, the primary object of the present invention is to provide a fluorescence detecting system which can obtain the auto-fluorescence information based on the auto-fluorescence and the fluorescence from the fluorescence agent information based on the fluorescence from the fluorescence agent from an object part which has been dosed with a fluorescence agent.

In accordance with the present invention, there is provided a fluorescence detecting system comprising a stimulating light projecting means which projects onto an object part which has been dosed with a fluorescence agent first stimulating light in the exciting wavelength range of the fluorescence agent and second stimulating light which differs from the first stimulating light in the wavelength band and is in the exciting wavelength range of the auto-fluorescence material contained in the object part, and a fluorescence information obtaining means which obtains the fluorescence from the fluorescence agent information based on the fluorescence from the fluorescence agent emitted from the object part in response to projection of the first stimulating light and the auto-fluorescence information based on the auto-fluorescence emitted from the object part in response to projection of the second stimulating light, wherein the fluorescence agent is a fluorescence agent which does not emit fluorescence in response to projection of the second stimulating light.

The first and second stimulating light may be projected either simultaneously or at different timings. Further "a fluorescence agent which does not emit fluorescence in response to projection of the second stimulating light" need not be limited to a fluorescence agent which does not emit fluorescence in response to projection of the second stimulating light but may be a fluorescence agent which emits in response to projection of the second stimulating light slight fluorescence from the fluorescence agent which substantially does not prevent the fluorescence information obtaining means from obtaining the auto-fluorescence.

When the wavelength range of the first stimulating light is not shorter than 700 nm and not longer than 800 nm, the wavelength range of the second stimulating light may be not shorter than 400 nm and not longer than 430 nm.

As a fluorescence agent which is excited by light not shorter than 700 nm and not longer than 800 nm and is not excited by light not shorter than 400 nm and not longer than 430 nm, and which does not adversely affect an organic body and accordingly can be dosed to the object part, an infra-red fluorescence shadowing agent comprising cyanine dye compounds containing therein sodium salt in which three or more sulfonic acid groups are introduced (disclosed in PCT Japanese Publication No. 2002-526458 (WO 2000/016810) or PCT Japanese Publication No. 2003-517025 (WO 01/043781)) can be listed.

The fluorescence detecting system of the present invention may further comprise a display means which displays fluorescence from the fluorescence agent information and auto-fluorescence information at one time.

Further, the fluorescence detecting system of the present invention may further comprise a determining means which determines the tissue properties of the object part on the basis of the fluorescence from the fluorescence agent information and the auto-fluorescence information.

The determining means may calculate a determination value by calculating an fluorescence from the fluorescence agent value reflecting the tissue properties of the object part on the basis of the fluorescence from the fluorescence agent information and an auto-fluorescence value reflecting the tissue properties of the object part on the basis of the auto-fluorescence information and by calculating the determination value according to one of the following formulae (1) and (2).

$$\text{determination value} = \text{auto-fluorescence value} \cdot w1 - \text{fluorescence from the fluorescence agent value} \cdot w2 \quad (1)$$

$$\text{determination value} = \text{auto-fluorescence value} \cdot w3 - (1/\text{fluorescence from the fluorescence agent value}) \cdot w4 \quad (2)$$

wherein $w1$, $w2$, $w3$ and $w4$ are weighting coefficients which have been set in advance.

The determining means may determine whether the object part is normal or diseased on the basis of the fluorescence from the fluorescence agent information, may determine whether the object part is normal or diseased on the basis of the auto-fluorescence information and may determine the tissue properties of the object part on the basis of the result of determination based on the fluorescence from the fluorescence agent and the result of determination based on the auto-fluorescence. In this case, the determining means may determine that the object part is normal when the result of determination based on the fluorescence from the fluorescence agent and the result of determination based on the auto-fluorescence both say that the object part is normal and otherwise that the object part is diseased. Or the determining means may determine that the object part is diseased when the result of determination based on the fluorescence from the fluorescence agent and the result of determination based on the auto-fluorescence both say that the object part is diseased and otherwise that the object part is normal.

Otherwise, the determining means may determine that the object part is diseased when the result of determination based on the fluorescence from the fluorescence agent and the result of determination based on the auto-fluorescence both say that the object part is diseased, that the probability that the object part is diseased is strong when the result of determination based on the fluorescence from the fluorescence agent says that the object part is diseased and the result of determination based on the auto-fluorescence says that the object part is normal, that the probability that the object part is diseased is intermediate when the result of determination based on the fluorescence from the fluorescence agent says that the object part is normal and the result of determination based on the auto-fluorescence say that the object part is diseased, and that the object part is normal when the result of determination based on the fluorescence from the fluorescence agent and the result of determination based on the auto-fluorescence both say that the object part is normal.

The fluorescence information obtaining means may have an image taking means which two-dimensionally images fluorescence emitted from the object part. Further, the fluorescence information obtaining means may have a spectrum detecting means which detects a spectrum of fluorescence emitted from the object part.

The fluorescence detecting system of the present invention may be in the form of an endoscope which is inserted into an organic body through a cavity in the organic body.

Since the fluorescence detecting system in accordance with the present invention comprises a stimulating light projecting means which projects onto an object part which has been dosed with a fluorescence agent first stimulating light in the exciting wavelength range of the fluorescence agent and second stimulating light which differs from the first stimulating light in the wavelength band and is in the exciting wavelength range of the auto-fluorescence material contained in the object part, and a fluorescence information obtaining means which obtains the fluorescence from the fluorescence agent information based on the fluorescence from the fluorescence agent emitted from the object part in response to projection of the first stimulating light and the auto-fluorescence information based on the auto-fluorescence emitted from the object part in response to projection of the second stimulating light, and the fluorescence agent is a fluorescence agent which does not emit fluorescence in response to projection of the second stimulating light, mingling of the wavelength band of the fluorescence from the fluorescence agent and that of the auto-fluorescence can be prevented, and the auto-fluorescence information based on the auto-fluorescence and the fluorescence from the fluorescence agent information based on the fluorescence from the fluorescence agent can be discretely obtained by only one examination of the object part which has been dosed with a fluorescence agent.

Further, since the intensity of the fluorescence from the fluorescence agent is generally stronger than that of the auto-fluorescence, emission of the auto-fluorescence from the object part in response to projection of the first stimulating light does not interfere with obtaining the fluorescence from the fluorescence agent information. However, it is further preferred that the wavelength band of the first stimulating light be in the range where the auto-fluorescence is emitted less or none from the object part in response to projection of the first stimulating light.

When the wavelength range of the first stimulating light is not shorter than 700 nm and not longer than 800 nm and the wavelength range of the second stimulating light is not shorter than 400 nm and not longer than 430 nm, the auto-fluorescence is hardly emitted from the object part in response to projection of the first stimulating light and the fluorescence from the fluorescence agent information can be obtained at a high accuracy.

When the fluorescence detecting system of the present invention further comprises a display means which displays fluorescence from the fluorescence agent information and auto-fluorescence information at one time, the observer can simultaneously view fluorescence from the fluorescence agent information and auto-fluorescence information and can diagnosis the tissue properties more accurately on the basis of these two pieces of information.

Further, when the fluorescence detecting system of the present invention further comprises a determining means which determines the tissue properties of the object part on the basis of the fluorescence from the fluorescence agent information and the auto-fluorescence information, a highly reliable result of determination can be obtained.

Further, when the fluorescence detecting system calculates a determination value by calculating an fluorescence from the fluorescence agent value reflecting the tissue properties of the object part on the basis of the fluorescence from the fluorescence agent information and an auto-fluorescence value reflecting the tissue properties of the object part on the basis of the auto-fluorescence information and by calculating the determination value according to the following formula (1) or (2), a more reliable result of determination can be obtained.

$$\text{determination value} = \text{auto-fluorescence value} \cdot w1 - \text{fluorescence from the fluorescence agent value} \cdot w2 \quad (1)$$

$$\text{determination value} = \text{auto-fluorescence value} \cdot w3 - (1/\text{fluorescence from the fluorescence agent value}) \cdot w4 \quad (2)$$

wherein $w1$, $w2$, $w3$ and $w4$ are weighting coefficients which have been set in advance.

When the determining means determines whether the object part is normal or diseased on the basis of the fluorescence from the fluorescence agent information, determines whether the object part is normal or diseased on the basis of the auto-fluorescence information and determines the tissue properties of the object part on the basis of the result of determination based on the fluorescence from the fluorescence agent and the result of determination based on the auto-fluorescence, a highly reliable result of determination can be obtained.

When the determining means determines that the object part is diseased if the result of determination based on the fluorescence from the fluorescence agent and the result of determination based on the auto-fluorescence both say that the object part is diseased, that the probability that the object part is diseased is strong if the result of determination based on the fluorescence from the fluorescence agent says that the object part is diseased and the result of determination based on the auto-fluorescence says that the object part is normal, that the probability that the object part is diseased is intermediate if the result of determination based on the fluorescence from the fluorescence agent says that the object part is normal and the result of determination based on the auto-fluorescence say that the object part is diseased, and that the object part is normal if the result of determination based on the fluorescence from the fluorescence agent and the result of determination based on the auto-fluorescence both say that the object part is normal, a more reliable result of determination can be obtained.

When the fluorescence information obtaining means has an image taking means which two-dimensionally images fluorescence emitted from the object part, the fluorescence from the fluorescence agent information and the auto-fluorescence information can be obtained as a two-dimensional image.

When, the fluorescence information obtaining means has a spectrum detecting means which detects a spectrum of fluorescence emitted from the object part, the fluorescence from the fluorescence agent information and the auto-fluorescence information can be obtained from a desired point.

When the fluorescence detecting system of the present invention is in the form of an endoscope which is inserted into an organic body through a cavity in the organic body, the convenience of this system can be improved.

DESCRIPTION OF THE PREFERRED EMBODIMENTS

Fluorescence endoscopes in accordance with embodiments of the present invention will be described with reference to the drawings, hereinbelow. The fluorescence endoscope shown in FIG. 1 uses a fluorescence detecting system in accordance with a first embodiment of the present invention. This fluorescence endoscope obtains fluorescence from the fluorescence agent information and auto-fluorescence information from an object part which has been dosed with fluorescent agent and generates and displays a diagnostic fluorescence from the fluorescence agent image, a diagnostic auto-fluorescence image, a diagnostic superimposed fluorescence image and a diagnostic integrated fluorescence image on the basis of the fluorescence from the fluorescence agent information and the auto-fluorescence information as well as obtaining and displaying a common color image of the object part which has been dosed with fluorescent agent in advance which selectively accumulates on a diseased part.

Figure 1:
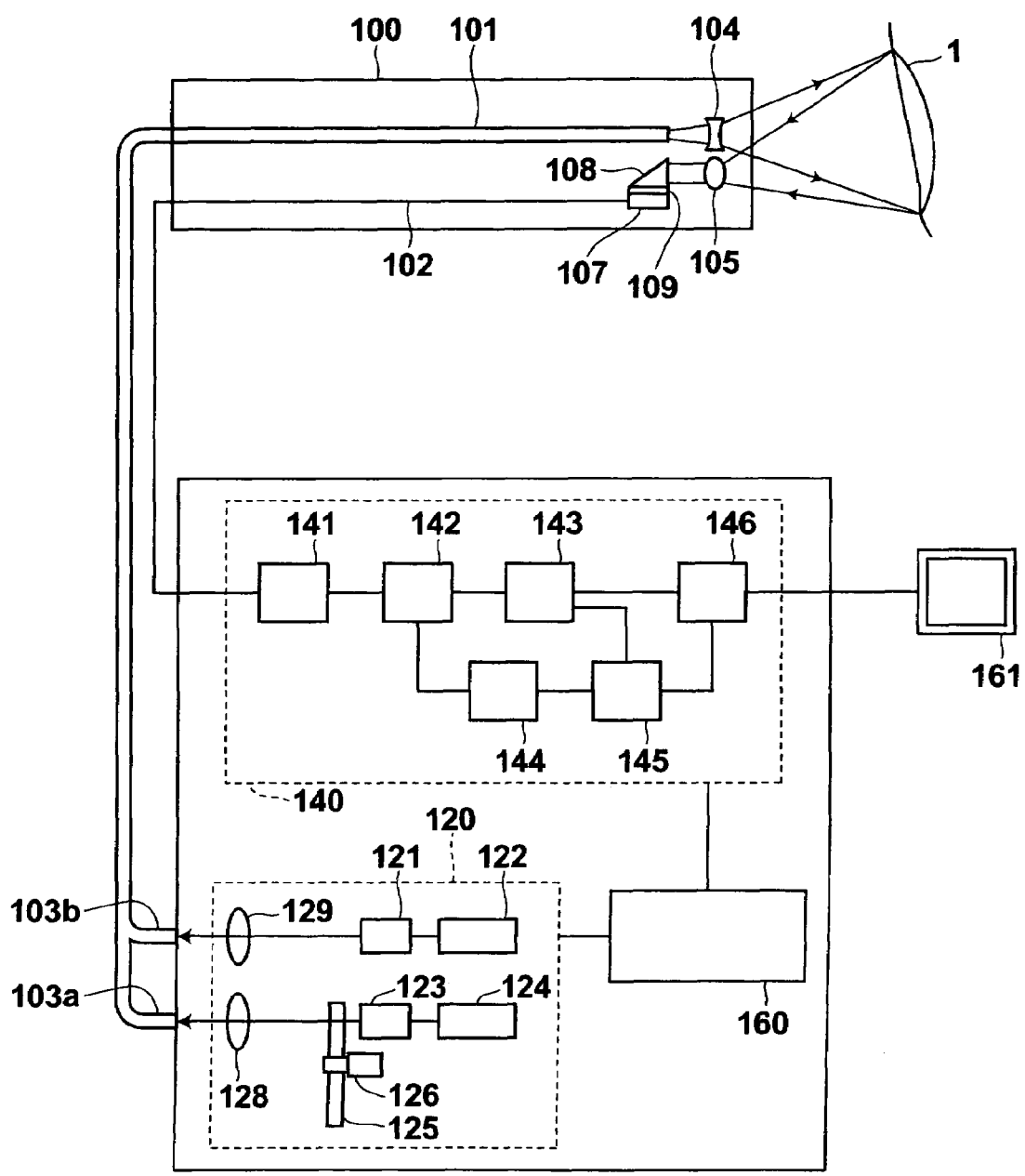
FIG. 1 is a block diagram showing the structure of a fluorescence endoscope in accordance with a first embodiment of the present invention.

As shown in FIG. 1, the fluorescence endoscope of the first embodiment is provided with a CCD 107 at its leading end and comprises an insertion portion 100 which is inserted into a suspected diseased part of a patient, an illumination unit 120 which emits white light Lw, IR light Li and stimulating light L1 for obtaining fluorescence from the fluorescence agent information, and stimulating light L2 for obtaining auto-fluorescence information, an image processing unit 140 which generates a common image, a diagnostic fluorescence from the fluorescence agent image, a diagnostic auto-fluorescence image, a diagnostic superimposed fluorescence image and a diagnostic integrated fluorescence image on the basis of the information obtained by the CCD 107, a controller 160 which is connected to the units and controls the timing of operation of the units, and a monitor 161 which displays each of the images as a visible image.

Figure 2:
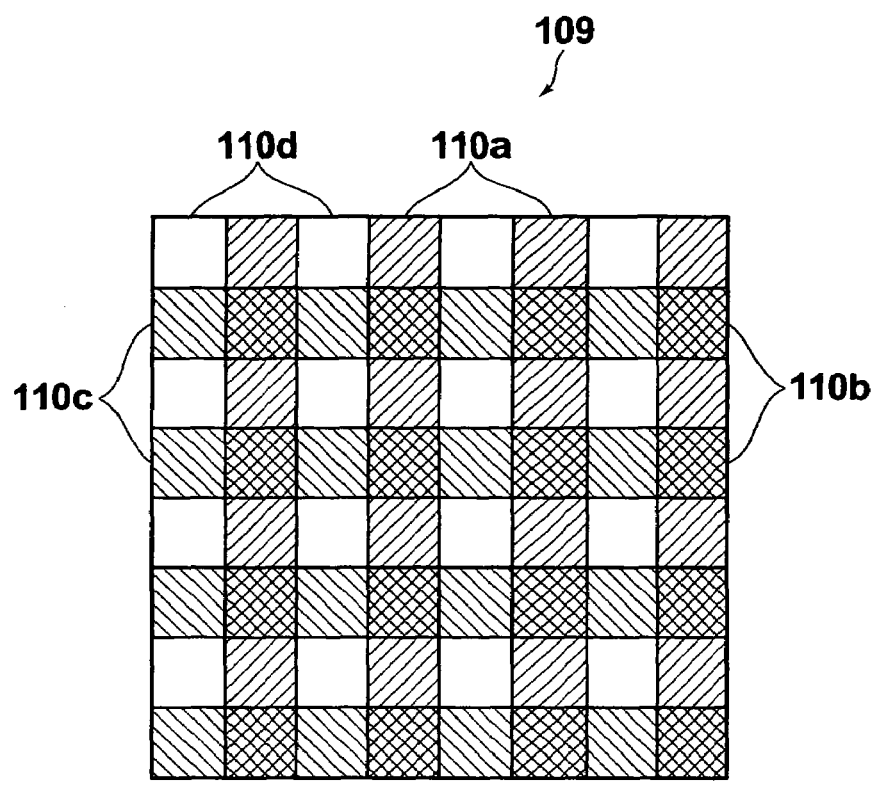
FIG. 2 is a view showing a mosaic filter.
Figure 3:
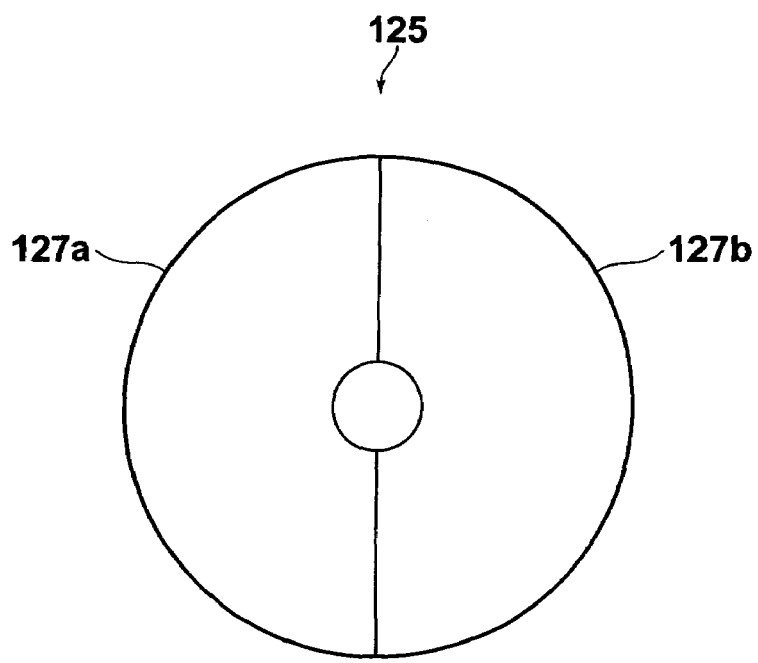
FIG. 3 is a view showing a switching filter.

The insertion portion 100 comprises a light guide 101 and a CCD cable 102. The light guide 101 and the CCD cable 102 extend inside the insertion portion 100 up to the front end of the endoscope. An illumination lens 104 and an objective lens 105 are provided on the front end of the light guide 101 and the CCD cable 102, that is, the front end of the insertion portion 100. The CCD 107 is connected to the front end of the CCD cable 102 and a mosaic filter 109 comprising a number of fine filters as shown in FIG. 2 is formed on the CCD 107 in on-chip.

The mosaic filter 109 comprises a plurality of R-filters 110a which transmit R light in a red region of 630 to 730 nm, a plurality of G-filters 110b which transmit G light in a green region of 530 to 630 nm, a plurality of B-filters 110c which transmit B light in a blue region of 430 to 530 nm, and a plurality of IR-filters 110d which transmit IR light in a near infrared region of 760 to 900 nm which are positioned in a mosaic so that each of the fine filters corresponds to one pixel of the CCD 107.

A prism 108 is mounted on the mosaic filter 109 so that an image is formed on the mosaic filter 109. The light guide 101 comprises a white/IR light guide 103a and a stimulating light guide 103b which are bundled together and integrated into a cable. The light guides 103a and 103b are connected to the illumination unit 120 and the CCD cable 102 is connected to the image processing unit 140 at its one end.

The illumination unit 120 comprises a semiconductor laser 121 provided with an AlGaAs semiconductor laser which emits the stimulating light L1 of a wavelength of 750 nm for obtaining fluorescence from the fluorescence agent and a Ga—N semiconductor laser which emits the stimulating light L2 of a wavelength of 410 nm for obtaining auto-fluorescence, a power source 122 for the light source, a xenon light source 123 emitting light from a visible region to an infrared region, a power source 124 for the xenon light source, a switching filter 125 for taking out white light Lw and IR light Li from the xenon light source and a filter rotating portion 126. The AlGaAs semiconductor laser and the Ga—N semiconductor laser are built in the semiconductor laser 121 and the stimulating light L1 and the stimulating light L2 are switched.

The fluorescence image processing unit 140 comprises an A/D converter 141 which digitizes a signal photoelectrically converted by the CCD 107, an image memory 142 which stores the digitized signals by the wavelength bands as image data, a common image generating portion 143 which generates common image data (image data to be displayed commonly) on the basis of reflected R image data, reflected G image data and reflected B image data stored in the image memory 142, a diagnostic fluorescence image generating portion 144 which generates each diagnostic fluorescence image data reflecting the tissue properties of the object part, a displayed image generating portion 145 which synthesizes each fluorescence image data reflecting the tissue properties of the object part and tissue shape image data reflecting the tissue shape of the object part to generate each displayed diagnostic fluorescence image data, and a video signal processing circuit 146 which converts the common image data generated by the common image generating portion 143 and each diagnostic fluorescence displayed image data generated by the displayed image generating portion 145 to video signals and outputs the video signals to the monitor 161.

Obtainment and generation of the common image and each diagnostic fluorescence image in the endoscope of this embodiment will be described, hereinbelow.

An examinee has been dosed with a fluorescence agent in advance. As a fluorescence agent, an infra-red fluorescence shadowing agent comprising cyanine dye compounds containing therein sodium salt in which three or more sulfonic acid groups are introduced (disclosed in PCT Japanese Publication No. 2002-526458 (WO2000/016810) is used. The fluorescence agent is excited by stimulating light not shorter than 700 nm and not longer than 800 nm to emit fluorescence in the wavelength range of 750 nm to 900 nm which is less in absorption by the organic body and is excellent in transmission. Though AlGaAs semiconductor laser the wavelength of which is 750 nm is used as a stimulating light source in this embodiment, AlGaInP semiconductor laser the wavelength of which is the same may be used as a stimulating light source.

Figure 4:
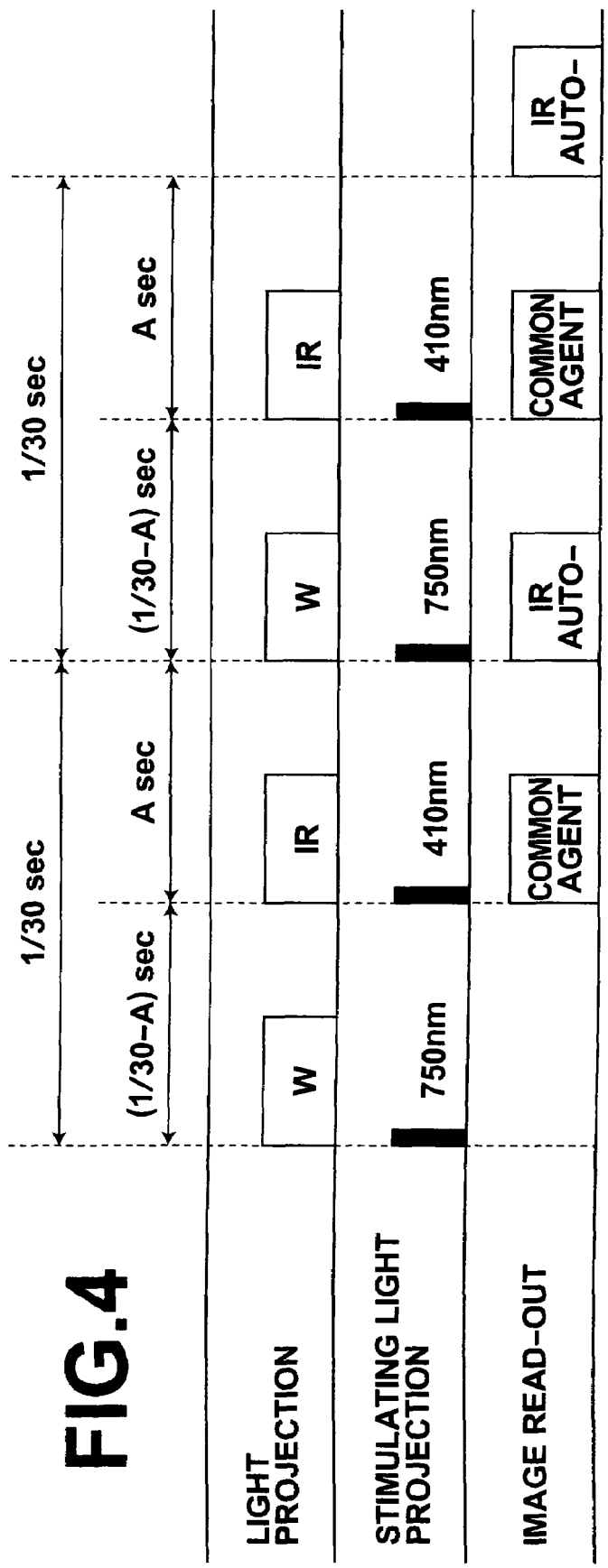
FIG. 4 is a view showing the timings.
Figure 5:
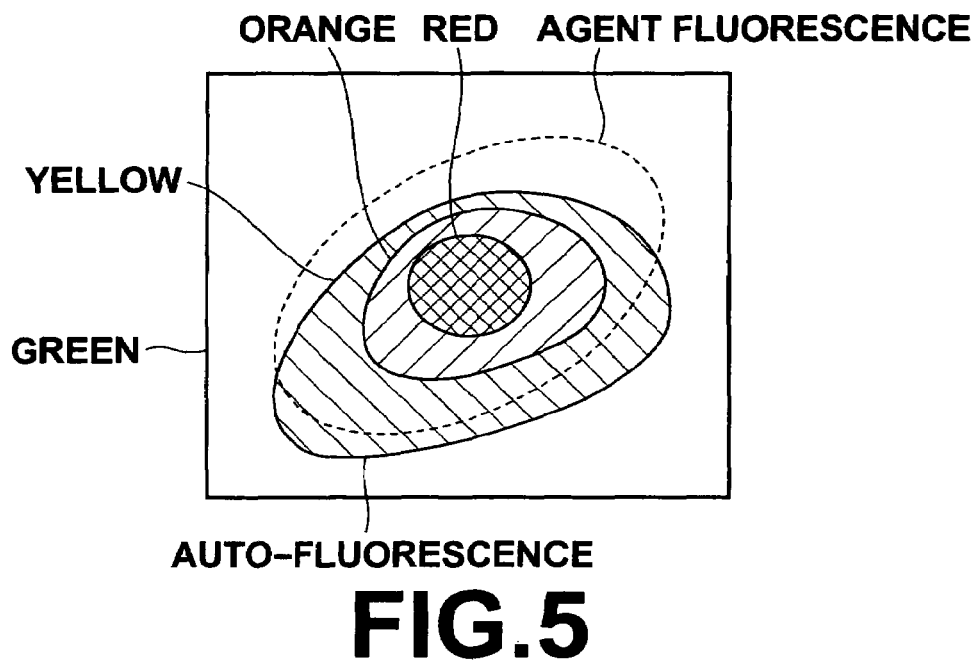
FIG. 5 is a view showing an image to be displayed.

As shown in FIG. 4, in this endoscope, the white light Lw and the stimulating light L1 and the IR light Li and the stimulating light L2 are alternatively projected onto the object part 1 in a time sharing manner to obtain common image information and fluorescence information under the control of the controller 160.

Projection of the white light Lw and the stimulating light L1 will be described first. Under the control of the controller 160, a W filter 127a of the switching filter 125 is positioned on the optical path to transmit the white light Lw. The xenon light source 123 is driven to emit xenon light by way of the xenon light power source 124. The xenon light is turned to white light Lw through the W filter 127a, travels by way of a collective lens 128 to enter the white/IR light guide 103a, guided to the front end of the endoscope and then is projected onto the object part 1 from the illumination lens 104. Reflected light L5 of the white light Lw is collected by the collective lens 105, is reflected by the prism 108 to be imaged on the CCD 107 and is received and photoelectrically converted by the CCD 107.

A mosaic filter 109 comprising a number of fine filters as shown in FIG. 2 is formed on the CCD 107 in on-chip. R light having a wavelength of 630 to 730 nm in the reflected light L5 (will be referred to as "reflected R light", hereinbelow) is transmitted through the R filters 110a and photoelectrically converted by the CCD 107 to be output to the image processing unit 140 as a reflected R image signal. The reflected R image signal is digitized by the A/D converter 141 in the image processing unit 140 and the digitized reflected R image signal is stored in the image memory 142 in the reflected R image storage region. Similarly, the G light transmitted through the G filters 110b (will be referred to as "reflected G light", hereinbelow) is photoelectrically converted by the CCD 107 and is stored in the image memory 142 in the reflected G image storage region as reflected G image data. The B light transmitted through the G filters 110c (will be referred to as "reflected B light", hereinbelow) is photoelectrically converted by the CCD 107 and is stored in the image memory 142 in the reflected B image storage region as reflected B image data.

Also the stimulating light L1 having a wavelength of 750 nm is projected onto the object part 1 in synchronization with projection of the white light Lw. Under the control of the controller 160, the laser light source 121 is driven to emit the stimulating light L1, and the stimulating light L1 is caused to enter the stimulating light guide 103b, guided to the front end of the endoscope and then projected onto the object part 1 from the illumination lens 104. Since the examinee has been dosed with a fluorescence agent in advance, the object part 1 emits fluorescence from the fluorescence agent L6 having a wavelength of not shorter than 760 nm. The fluorescence from the fluorescence agent L6 is collected by the collective lens 105, is reflected by the prism 108, is transmitted through the IR filters 110d, is imaged on the CCD 107 and is photoelectrically converted by the CCD 107 to be output to the image processing unit 140 as a IR fluorescence image signal. The IR fluorescence image signal is digitized by the A/D converter 141 in the image processing unit 140 and the digitized IR fluorescence image signal is stored in the image memory 142 in the IR fluorescence image storage region as IR fluorescence image data.

Projection of the IR light Li and the stimulating light L2 will be described next. Under the control of the controller 160, an IR filter 127b of the switching filter 125 is positioned on the optical path to transmit the IR light Li. The xenon light source 123 is driven to emit xenon light by way of the xenon light power source 124. The xenon light is turned to IR light Li through the IR filter 127b, travels by way of a collective lens 129 to enter the white/IR light guide 103b, guided to the front end of the endoscope and then is projected onto the object part 1 from the illumination lens 104. Reflected light L7 of the IR light Li is collected by the collective lens 105, is reflected by the prism 108, is transmitted through the IR filters 110d, is imaged on the CCD 107 and is photoelectrically converted by the CCD 107 to be output to the image processing unit 140 as a reflected IR image signal. The reflected IR image signal is digitized by the A/D converter 141 in the image processing unit 140 and the digitized reflected IR image signal is stored in the image memory 142 in the reflected IR image storage region as a reflected IR image signal.

Also the stimulating light L2 having a wavelength of 410 nm is projected onto the object part 1 in synchronization with projection of the IR light Li. Under the control of the controller 160, the laser light source 121 is driven to emit the stimulating light L2 and the stimulating light L2 is caused to enter the stimulating light guide 103b, guided to the front end of the endoscope and then projected onto the object part 1 from the illumination lens 104. The object part 1 emits auto-fluorescence LB having a wavelength of not shorter than 430 nm. The auto-fluorescence LB is collected by the collective lens 105, is reflected by the prism 108, is imaged on the CCD 107 and is photoelectrically converted by the CCD 107. R light having a wavelength of 630 to 730 nm in the auto-fluorescence LB (will be referred to as "R fluorescence light", hereinbelow) is transmitted through the R filters 110a and photoelectrically converted by the CCD 107 to be output to the image processing unit 140 as an R fluorescence image signal. The R fluorescence image signal is digitized by the A/D converter 141 in the image processing unit 140 and the digitized R fluorescence image signal is stored in the image memory 142 in the R fluorescence image storage region as R fluorescence image data. Similarly, the G light transmitted through the G filters 110b (will be referred to as "G fluorescence light", hereinbelow) is photoelectrically converted by the CCD 107 and is stored in the image memory 142 in the G fluorescence image storage region as G fluorescence image data. The B light transmitted through the B filters 110c (will be referred to as "B fluorescence light", hereinbelow) is photoelectrically converted by the CCD 107 and is stored in the image memory 142 in the B fluorescence image storage region as B fluorescence image data.

Since the reflected light of the stimulating light L2 having a wavelength of 410 nm is cut by the B filters 110c and the reflected light of the stimulating light L1 having a wavelength of 750 nm is cut by the R filters 110a and the IR filters 110d and accordingly they do not affect obtainment of the fluorescence image data.

When the image data is stored in the image memory 142, the common image generating portion 143 generates common image data and the displayed image generating portion 145 generates each displayed diagnostic fluorescence image data at a display timing. These pieces of image data are output to the monitor 161 by way of the video signal processing circuit 146. As shown in FIG. 4, these images are updated every 1/30 seconds to be displayed as animation.

In the common image generating portion 143, common image data is generated on the basis of the reflected R image data, the reflected G image data, the reflected B image data stored in the image memory 142 as in the common color image data.

In the diagnostic fluorescence image generating portion 144 one or more pieces of diagnostic fluorescence image data is generated out of the diagnostic fluorescence from the fluorescence agent image data, diagnostic auto-fluorescence image data, diagnostic superimposed fluorescence image data and the integrated diagnostic fluorescence image data on the user's selection.

Generation of the diagnostic fluorescence from the fluorescence agent image data will be described first. The diagnostic fluorescence image generating portion 144 generates fluorescence from the fluorescence agent calculating image data pixel to pixel by dividing the value of each pixel represented by the IR fluorescence image data stored in the IR fluorescence image storage region of the image memory 142 by that of the reflected IR image data stored in the reflected IR image storage region of the image memory 142. The fluorescence from the fluorescence agent calculating image data reflects the tissue properties of the object part. The diagnostic fluorescence from the fluorescence agent image data is generated by setting a chromaticity so that chromaticity points on the locus of the B-C-y-R series in a XYZ color specification system correspond to small to large of the values of the pixels of the fluorescence from the fluorescence agent calculating image data by the use of lookup table which has been stored in advance. The diagnostic fluorescence from the fluorescence agent image data is data where the tissue properties are reflected on the chromaticity and does not reflect the tissue shape of the object part. The diagnostic fluorescence from the fluorescence agent image data is output to the displayed image generating portion 145. Though the value of each pixel represented by the IR fluorescence image data is divided by the value of the pixel represented by the reflected IR image data which is in the same wavelength bands as the fluorescence from the fluorescence agent in this embodiment in order to correct fluctuation and the like in the distance between the light source and the object part 1, the present invention need not be limited to such an arrangement. For example, near infrared rays having a wavelength of 1.3 μm or so which is less affected by an organic body may be projected onto the object part 1 to take an image of the reflected light thereof to use it as the reflected IR image data.

In the displayed image generating portion 145, a brightness is generated so that the brightness of each pixel corresponds to the value of the pixel represented by the reflected IR image data and the tissue shape image data reflecting the tissue shape of the object part is generated. Further, the fluorescence from the fluorescence agent image data reflecting the tissue properties of the object part and tissue shape image data reflecting the tissue shape of the object part are synthesized to generate each displayed diagnostic fluorescence from the fluorescence agent image data, where the viewer can simultaneously view both the tissue properties and the tissue shape, and the displayed diagnostic fluorescence from the fluorescence agent image data is output to the video signal processing circuit 146. The video signal processing circuit 146 converts the displayed diagnostic fluorescence from the fluorescence agent image data to a video signal and displays it on the monitor 161 as diagnostic fluorescence from the fluorescence agent images.

Since the fluorescence agent has tumor affinity as described above, strong fluorescence from the fluorescence agent is emitted from the diseased part of the object part 1 and fluorescence from the fluorescence agent is hardly emitted from the normal part of the object part 1. Accordingly, when the B-C-y-R chromaticity is caused to correspond to small to large of the values of the pixels of the fluorescence from the fluorescence agent calculating image data, the normal part where no fluorescence from the fluorescence agent is emitted is displayed in blue (B) and the diseased part where fluorescence from the fluorescence agent is emitted is displayed in red (R), whereby the observer can recognize the diseased part.

The diagnostic fluorescence from the fluorescence agent image data need not be of an image having a continuous change in its chromaticity but may be an image data of a gradation display system where change in the values of the pixels of the fluorescence from the fluorescence agent calculating image data (small to large) is divided into of a normal part, a suspicious normal part, a suspicious diseased part and a diseased part and blue, blue purple, purple and red are allotted to the respective parts. Otherwise, the diagnostic fluorescence from the fluorescence agent image data may be an image data of an area display system where an area of the diseased part or the diseased part plus the suspicious diseased part is circumscribed with a dotted line.

Though image data where the brightness of each pixel corresponds to the value of the pixel represented by the reflected IR image data is used as the tissue shape image data, the tissue shape image data need not be limited to such image data but, for instance, a brightness image (a white-and-black image) of the common image data may be used as the tissue shape image data.

Further, the common image data may be synthesized with the diagnostic fluorescence image data to the diagnostic fluorescence from the fluorescence agent image data.

Generation of the diagnostic auto-fluorescence image will be described next. The diagnostic fluorescence image generating portion 144 divides the value of each pixel represented by the B fluorescence image data by that of the reflected B image data. This will be referred to as "B fluorescence/reflected B", hereinbelow. Further, the diagnostic fluorescence image generating portion 144 calculates R fluorescence/reflected R by dividing the value of each pixel represented by the R fluorescence image data by that of the reflected R image data, and G fluorescence/reflected G by dividing the value of each pixel represented by the G fluorescence image data by that of the reflected G image data. Then the R fluorescence/reflected R, G fluorescence/reflected G and the B fluorescence/reflected B are summed up. The value thus obtained will be referred to as "RGB fluorescence/reflected RGB", hereinbelow. Then auto-fluorescence calculating image data is generated by dividing the B fluorescence/reflected B by the RGB fluorescence/reflected RGB. The auto-fluorescence calculating image data reflects the tissue properties of the object part 1. The diagnostic auto-fluorescence image data is generated by setting a chromaticity so that chromaticity points on the locus of the G-Y-R series in a XYZ color specification system correspond to small to large of the values of the pixels of the auto-fluorescence calculating image data by the use of lookup table which has been stored in advance. The diagnostic auto-fluorescence image data is data where the tissue properties are reflected on the chromaticity and does not reflect the tissue shape of the object part. The diagnostic auto-fluorescence image data is output to the displayed image generating portion 145.

Though the value of each pixel represented by each fluorescence image data is divided by the value of the pixel represented by the reflected image data and the B fluorescence/reflected B is divided by the RGB fluorescence/reflected RGB in this embodiment in order to suppress the influence of strain of the fluorescence spectrum due to scatter or the like, it is possible as in the conventional to generate the auto-fluorescence calculating image data by simply dividing the value of each pixel represented by the B fluorescence image data by the sum of the values of each pixel represented by the R fluorescence image data, G fluorescence image data and the B fluorescence image data. Further, calculation of the auto-fluorescence calculating image data need not be limited to the above mentioned division but may be any so long as it reflects the shape of the spectrum of the auto-fluorescence. For example, the auto-fluorescence calculating image data may be calculated by dividing the value of the pixel represented by the B fluorescence by the value of the pixel represented by the R fluorescence or by dividing the value of the pixel represented by the R fluorescence by the value of the pixel represented by the B fluorescence. When the auto-fluorescence calculating image data is calculated by dividing the value of the pixel represented by the R fluorescence by the value of the pixel represented by the B fluorescence, chromaticity points on the locus of the G-Y-R series in a XYZ color specification system are caused to continuously correspond to small to large of the values of the pixels of the auto-fluorescence calculating image data thus obtained.

In the displayed image generating portion 145, a brightness is set so that the brightness of each pixel corresponds to the value of the pixel equal to the value of the sum of the value of the pixel represented by the reflected R image data, the value of the pixel represented by the reflected G image data and the value of the pixel represented by the reflected B image data and the tissue shape image data reflecting the tissue shape of the object part is generated. Further, the auto-fluorescence image data reflecting the tissue properties of the object part and the tissue shape image data reflecting the tissue shape of the object part are synthesized to generate each displayed diagnostic auto-fluorescence image data, where the viewer can simultaneously view both the tissue properties and the tissue shape, and the displayed diagnostic auto-fluorescence image data is output to the video signal processing circuit 146. The video signal processing circuit 146 converts the displayed diagnostic auto-fluorescence image data to a video signal and displays it on the monitor 161 as diagnostic auto-fluorescence images.

Since the proportion of light in the B wavelength band is large in the auto-fluorescence when the object part is normal as described above, when the G-Y-R chromaticity is caused to continuously correspond to small to large of the values of the pixels of the auto-fluorescence calculating image data, the normal part where the proportion of light in the B wavelength band is large is displayed in green (G) and the diseased part where the proportion of light in the B wavelength band is small is displayed in red (R), whereby the observer can recognize the diseased part.

The diagnostic auto-fluorescence image data need not be of an image having a continuous change in its chromaticity but may be an image data of a gradation display system where change in the values of the pixels of the auto-fluorescence calculating image data (small to large) is divided into of a normal part, a suspicious normal part, a suspicious diseased part and a diseased part and blue, blue purple, purple and red are allotted to the respective parts. Otherwise, the diagnostic fluorescence from the fluorescence agent image data may be an image data of an area display system where an area of the diseased part or the diseased part plus the suspicious diseased part is circumscribed with a dotted line.

Though image data where the brightness of each pixel corresponds to the value of the pixel equal to the value of the sum of the value of the pixel represented by the reflected R image data, the value of the pixel represented by the reflected G image data and the value of the pixel represented by the reflected B image data is used as the tissue shape image data, the tissue shape image data need not be limited to such image data but, for instance, an image data where the brightness is set to correspond to the value of the pixel represented by the reflected IR image data or a brightness image (a white-and-black image) of the common image data may be used as the tissue shape image data.

Further, the common image data may be synthesized with the diagnostic auto-fluorescence image data to the diagnostic auto-fluorescence image.

It is preferred that the diagnostic auto-fluorescence image and the diagnostic fluorescence from the fluorescence agent image be simultaneously displayed on the monitor 161 in parallel.

Generation of the diagnostic superimposed fluorescence image, where the diagnostic auto-fluorescence image and the diagnostic fluorescence from the fluorescence agent image are superimposed, will be described next. The diagnostic fluorescence image generating portion 144 first generates the diagnostic auto-fluorescence image and the diagnostic fluorescence from the fluorescence agent image and superimposes these images to form the diagnostic superimposed fluorescence image. When the diagnostic fluorescence from the fluorescence agent image and the diagnostic auto-fluorescence image are superimposed, one of them may be in the form of the tissue property image data. Otherwise, a brightness image (a white-and-black image) of the common image data may be used as the tissue shape image data while both the diagnostic auto-fluorescence image and the diagnostic fluorescence from the fluorescence agent image are in the form of the tissue property image data. The tissue property image data need not be of an image having a continuous change in its chromaticity but may be an image data of a gradation display system or of an area display system. For example, the brightness image (a white-and-black image) of the common image data may be used as the tissue shape image data while image data where the diagnostic fluorescence from the fluorescence agent image data in the area display system is superimposed on the diagnostic auto-fluorescence image data in the gradation display system is used as the tissue property image data as shown in FIG.

Generation of the integrated fluorescence image will be described next. The diagnostic fluorescence image generating portion 144 first generates the auto-fluorescence calculating image data and the fluorescence from the fluorescence agent calculating image data described above. The value of each pixel represented by the fluorescence from the fluorescence agent calculating image data will be referred to as "the fluorescence from the fluorescence agent calculating value" and the value of each pixel represented by the auto-fluorescence calculating image data will be referred to as "the auto-fluorescence calculating value", hereinbelow. Then the determination value is calculated by the corresponding pixels according to the following formulae (1) and a fluorescence determining image data having the value as the value of each pixel is generated.

$$\text{determination value} = \text{auto-fluorescence value} \cdot w1 - \text{fluorescence from the fluorescence agent value} \cdot w2 \quad (1)$$

wherein $w1$, and $w2$ are weighting coefficients which have been set to an optimal value on the basis of object parts whose tissue properties are known.

Figure 6:
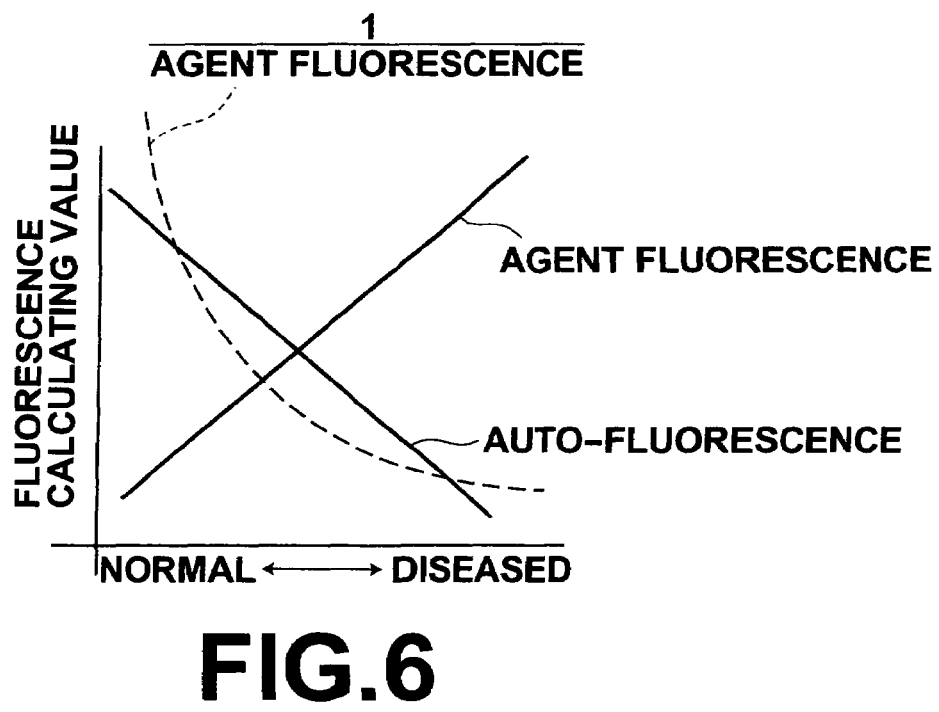
FIG. 6 is a view showing the fluorescence values.

The auto-fluorescence calculating value and the fluorescence from the fluorescence agent calculating value are represented by lines which are opposite to each other in the inclination as shown in FIG. 6 and the determination value reflects the tissue properties of the object part. The fluorescence determining image data is generated by setting a chromaticity so that chromaticity points on the locus of the B-G-R series in a XYZ color specification system correspond to small to large of the values of the pixels of the fluorescence determining image data by the use of lookup table which has been stored in advance. The fluorescence determining image data is data where the tissue properties are reflected on the chromaticity and does not reflect the tissue shape of the object part. The fluorescence determining image data is output to the displayed image generating portion 145. Calculation of the fluorescence determining image data need not be limited to according to the above formula but may be any so long as it reflects the tissue properties with the fluorescence from the fluorescence agent calculating value and the auto-fluorescence calculating value integrated with each other.

For example, the determination value may be calculated according to the following formula (2).

$$\text{determination value} = \text{auto-fluorescence value} \cdot w3 - (1/\text{fluorescence from the fluorescence agent value}) \cdot w4 \quad (2)$$

wherein $w3$ and $w4$ are weighting coefficients.

The auto-fluorescence calculating value and (1/fluorescence from the fluorescence agent value) are represented by lines which are the same in the inclination as shown in FIG. 6 and the determination value also reflects the tissue properties of the object part.

In the displayed image generating portion 145, brightness is set so that the brightness of each pixel corresponds to the value of the pixel equal to the value of the sum of the value of the pixel represented by the reflected R image data, the value of the pixel represented by the reflected G image data and the value of the pixel represented by the reflected B image data and tissue shape image data reflecting the tissue shape of the object part is generated. Further, the tissue shape image data and the determination value reflecting the tissue shape of the object part are synthesized to generate displayed fluorescence determination image data, where the viewer can simultaneously view both the tissue properties and the tissue shape, and the displayed fluorescence determination image data is output to the video signal processing circuit 146. The video signal processing circuit 146 converts the displayed fluorescence determination image data to a video signal and displays it on the monitor 161 as a fluorescence determination image.

As can be seen from FIG. 6, the determination value becomes large when the object part is normal and becomes small when the object part is diseased. Accordingly, when the B-G-R chromaticity is caused to correspond to change in small to large of the values of the pixels of the fluorescence determination image data, the normal part is displayed in blue (B) and the diseased part is displayed in red (R), and as the tissue properties changes from the normal to the diseased, the displaying color changes B-G-R, whereby the observer can easily recognize the diseased part.

The fluorescence determination image data need not be of an image having a continuous change in its chromaticity but may be an image data of a gradation display system where change in the values of the pixels of the fluorescence determination image data (small to large) is divided into of a normal part, a suspicious normal part, a suspicious diseased part and a diseased part and green, yellow, orange and red are allotted to the respective parts. Otherwise, the diagnostic fluorescence from the fluorescence agent image data may be an image data of an area display system where an area of the diseased part or the diseased part plus the suspicious diseased part is circumscribed with a dotted line or the like.

Further, as the tissue shape data, an image data, where brightness is set so that the brightness of each pixel corresponds to the value of the pixel equal to the value of the sum of the value of the pixel represented by the reflected R image data, the value of the pixel represented by the reflected G image data and the value of the pixel represented by the reflected B image data, the present invention need not be limited to the arrangement. For example, an image data, where brightness is set so that the brightness of each pixel corresponds to the value of the pixel represented by the reflected IR image data may used or the brightness image (a white-and-black image) of the common image data may be used as the tissue shape image data.

Further, the common image data may be synthesized with the fluorescence determination image data to the fluorescence determination image.

As can be understood from the description above, since the fluorescence agent used in the fluorescence detecting system of the present invention is a fluorescence agent which is excited by the stimulating light L1 having a wavelength of 750 nm but is not excited by the stimulating light L2 having a wavelength of 410 nm, mingling of the wavelength band of the fluorescence from the fluorescence agent and that of the auto-fluorescence can be prevented, and the auto-fluorescence information based on the auto-fluorescence and the fluorescence from the fluorescence agent information based on the fluorescence from the fluorescence agent can be discretely obtained by only one examination of the object part 1 which has been dosed with a fluorescence agent.

Further, since the wavelength band of the stimulating light L1 is 750 nm and the wavelength band of the stimulating light L2 is 410 nm, the auto-fluorescence is hardly emitted from the object part 1 in response to projection of the stimulating light L1 and the fluorescence from the fluorescence agent information can be obtained at a high accuracy.

Further, since the displayed diagnostic auto-fluorescence image and the displayed diagnostic fluorescence from the fluorescence agent image can be displayed on the monitor 161 in parallel or in a superimposed state, the observer can simultaneously recognize fluorescence from the fluorescence agent information and auto-fluorescence information and can diagnosis the tissue properties more accurately on the basis of these two pieces of information.

Since, the fluorescence from the fluorescence agent calculating value reflecting the tissue properties of the object part 1 on the basis of the fluorescence from the fluorescence agent information is calculated, the auto-fluorescence calculating value reflecting the tissue properties of the object part 1 on the basis of the auto-fluorescence information is calculated, and the determination value is calculated according to the following formula (1), a more reliable determination value can be obtained.

$$\text{determination value} = \text{auto-fluorescence value} \cdot w1 - \text{fluorescence from the fluorescence agent value} \cdot w2 \quad (1)$$

wherein w1, and w2 are weighting coefficients which have been set in advance.

A fluorescence endoscope in accordance with a second embodiment of the present invention employing a fluorescence detecting system of the present invention will be described with reference to FIG. 7, hereinbelow. In the fluorescence endoscope in accordance with this embodiment, a spectrum detecting portion which detects a spectrum of the auto-fluorescence emitted from the object part 1 and a spectrum of the fluorescence from the fluorescence agent emitted from the object part 1 and a determining portion which determines the tissue properties on the basis of the spectrum of the auto-fluorescence are added to the fluorescence endoscope in accordance with the first embodiment. In this embodiment, the elements analogous to those of the first embodiment shown in FIG. 1 are given the same reference numerals and will not be described unless necessary.

Figure 7:
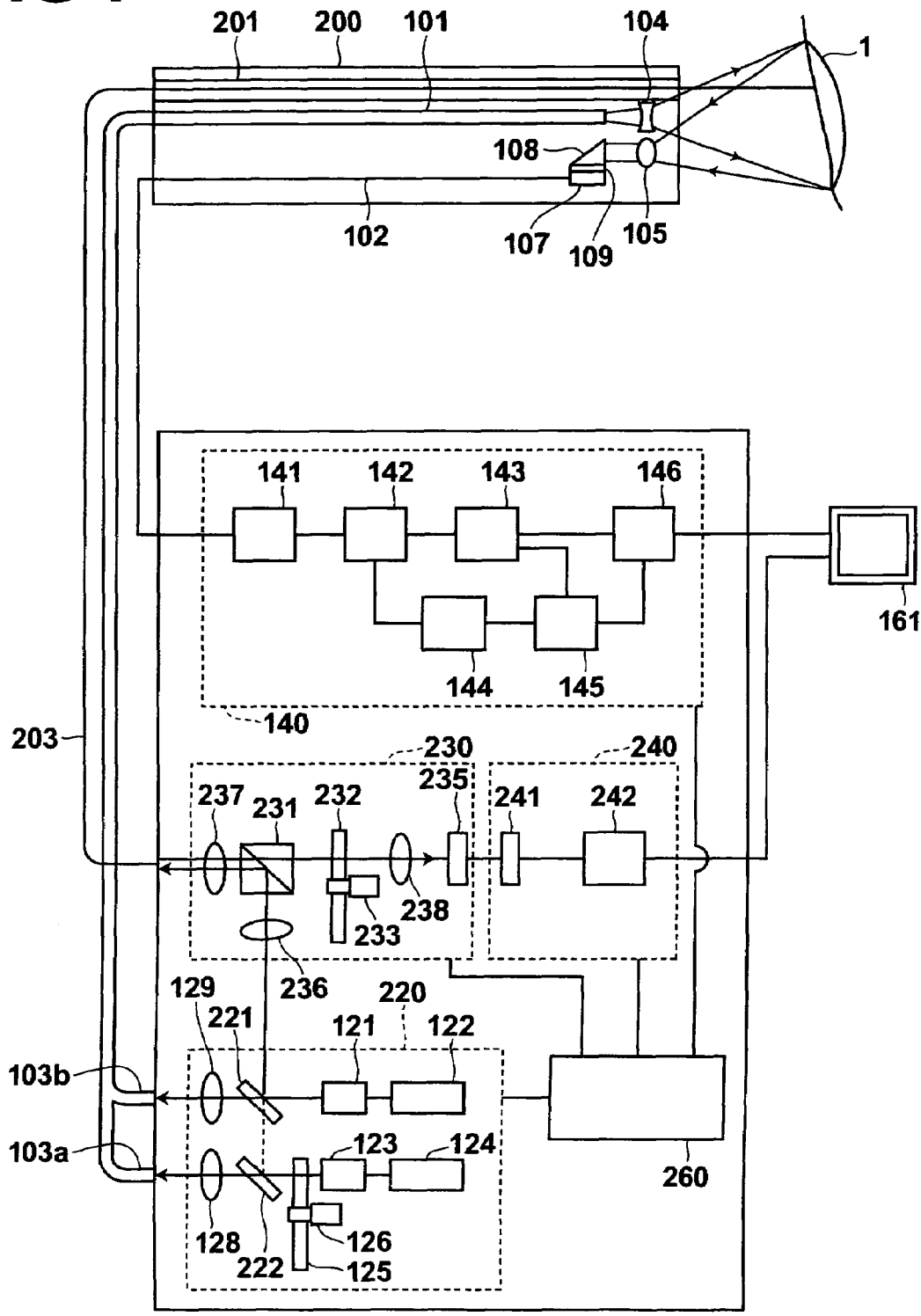
FIG. 7 is a block diagram showing the structure of a fluorescence endoscope in accordance with a second embodiment of the present invention.
Figure 8:
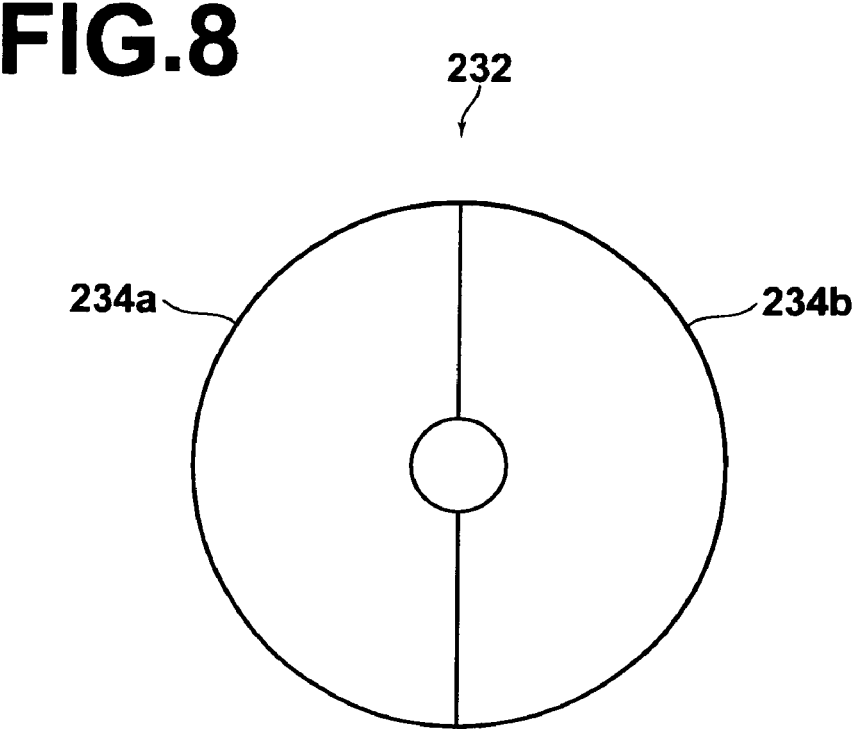
FIG. 8 is a view showing a switching filter.
Figure 9:
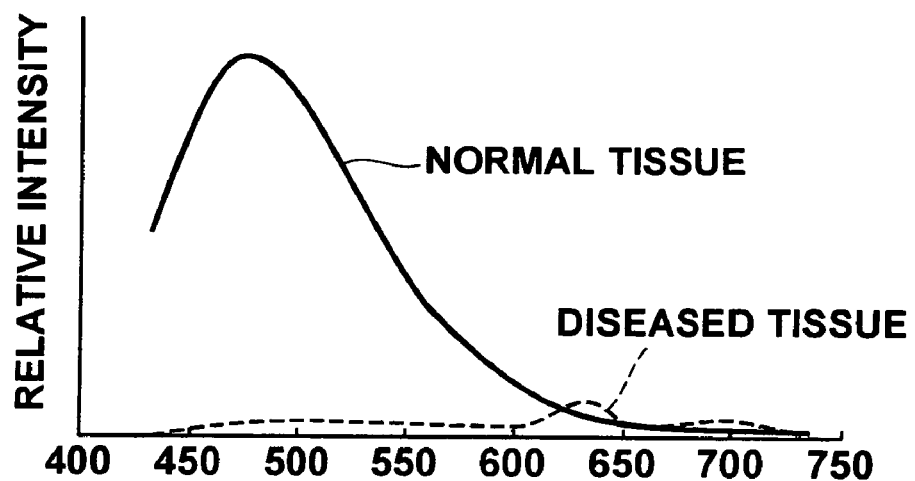
FIG. 9 is a view showing the characteristics of the spectrum of the auto-fluorescence emitted from a normal tissue and a diseased tissue.

As shown in FIG. 7, the fluorescence endoscope in accordance with this embodiment comprises an endoscope insertion portion 200 provided with a forceps port 201, a quartz fiber 203 which is inserted into the forceps port 201, an illumination unit 220 which radiates white light Lw, IR light Li and stimulating light L1 for obtaining auto-fluorescence information, and stimulating light L2 for obtaining fluorescence from the fluorescence agent information to light guides or the quartz fiber 203, an image processing unit 140 which generates a common image, a diagnostic fluorescence from the fluorescence agent image, a diagnostic auto-fluorescence image, a diagnostic superimposed fluorescence image and a diagnostic integrated fluorescence image on the basis of the image information obtained by the CCD 107, a spectrum detecting unit 230 which detects a spectrum of the fluorescence, a determination unit 240, a controller 260 which is connected to the units and controls the timing of operation of the units, and a monitor 161 which displays each of the images as a visible image.

The illumination unit 220 comprises a semiconductor laser 121 which switches the stimulating light L1 of a wavelength of 750 nm for obtaining fluorescence from the fluorescence agent and the stimulating light L2 of a wavelength of 410 nm for obtaining auto-fluorescence, a power source 122 for the light source, a xenon light source 123 emitting light from a visible region to an infrared region, a power source 124 for the xenon light source, a switching filter 125 for taking out white light Lw and IR light Li from the xenon light, a filter rotating portion 126 and a pair of switching mirrors 221 and 222 for switching the optical path of the light to the light guides 103a and 103b or the quartz fiber 203.

The spectrum detecting unit 230 comprises a half-silvered mirror 231 which causes light output from the illumination unit 220 to enter the quartz fiber 203 and causes light to travel to a spectroscope 235, a switching filter 232 and a filter rotating portion 233.

The switching filter 232 comprises a w-filter 234a which transmits white light Lw in a wavelength band of 430 to 730 nm and an IR-filter 234b which transmits IR light in a wavelength band of 760 to 900 nm.

The determination unit 240 comprises a memory 241 which stores the spectrum detected by the spectroscope 235 and a determination portion 242 which determines the tissue properties on the basis of the spectrum stored in the memory 241.

The observer observes the common image and the diagnostic fluorescence image displayed by operation similar to that in the first embodiment to select the part in the object part 1 from which the fluorescence spectrum is to be obtained in order to determine the tissue properties and manually leads the front end of the quartz fiber 203 to the part.

The controller 260 is first controlled to position the switching mirrors 221 and 222 on the optical path so that light emitted from each light source in the illumination unit 220 enters the quartz fiber 203.

Further, the IR filter 234b of the switching filter 232 of the spectrum detecting unit 230 which transmits light having a wavelength of 760 to 900 nm is positioned on the optical path. Then the stimulating light L1 having a wavelength of 750 nm is emitted. The stimulating light L1 propagates through the quartz fiber 203 and is radiated to the object part 1. The fluorescence from the fluorescence agent emitted from the object part 1 propagates through the quartz fiber 203 and enters the spectroscope 235 passing through the half-silvered mirror 231 and the IR-filter 234b of the spectrum detecting unit 230. The spectrum of fluorescence from the fluorescence agent detected by the spectroscope 235 is stored in the memory 241.

Then the controller 260 causes the illumination unit 220 to emit IR light Li and obtains the spectrum of the fluorescence of the reflected IR light. The spectrum of the fluorescence of the reflected IR light is also stored in the memory 241.

Thereafter, the W filter 234a of the switching filter 232 of the spectrum detecting unit 230 which transmits light having a wavelength of 430 to 730 nm is positioned on the optical path and causes the illumination unit 220 to emit the stimulating light L2 having a wavelength of 410 nm. The stimulating light L2 is collected by the lens 236 and normally reflected by the half-silvered mirror 231 to enter the quartz fiber 203 by way of the lens 237. The stimulating light L2 thereafter propagates through the quartz fiber 203 and is radiated to the object part 1. The auto-fluorescence emitted from the object part 1 propagates through the quartz fiber 203 and is collected on the spectroscope 235 passing through the half-silvered mirror 231 and the W-filter 234b of the spectrum detecting unit 230. The spectrum of fluorescence from the fluorescence agent detected by the spectroscope 235 is output to the memory 241.

Then the controller 260 causes the illumination unit 220 to emit white light Lw and obtains the spectrum of the fluorescence of the reflected white light Lw. The spectrum of the fluorescence of the reflected white light is also stored in the memory 241.

Determination of the tissue properties on the basis of fluorescence from the fluorescence agent will be described first. In the determination portion 242, the intensity of light A1 is first calculated from the spectrum of fluorescence from the fluorescence agent, and the intensity of light A2 of the reflected IR light is calculated from the spectrum of the reflected IR light. Then the intensity of light A1 is divided by the intensity of light A2 to obtain the divided value A3, and when the divided value A3 is larger than a reference value A4 which is set on the basis of measuring data obtained from the object parts whose tissue properties are known, it is determined that the tissue is diseased from determination on the basis of fluorescence from the fluorescence agent. When the former is not larger than the latter, it is determined that the tissue is normal from determination on the basis of fluorescence from the fluorescence agent.

Determination of the tissue properties on the basis of auto-fluorescence will be described next. In order to suppress the influence of strain of the fluorescence spectrum due to scatter or the like, the spectrum of auto-fluorescence stored in the memory 241 is divided by the spectrum of the fluorescence of the reflected white light Lw stored in the memory 241 by the wavelengths. By this division, a corrected spectrum of auto-fluorescence is obtained. Further, the intensity of the whole spectrum of auto-fluorescence is divided by the intensity of the whole spectrum of the fluorescence of the reflected white light Lw. By this division, the whole intensity of a corrected spectrum of auto-fluorescence is obtained.

Thereafter, the intensity of light having a wavelength of 480 nm in the corrected spectrum of auto-fluorescence is divided by the whole intensity of the corrected spectrum of auto-fluorescence. When the divided value B1 is smaller than a reference value B2 which is set on the basis of measuring data obtained from the object parts whose tissue properties are known, it is determined that the tissue is diseased from determination on the basis of auto-fluorescence. When the former is not smaller than the latter, it is determined that the tissue is normal from determination on the basis of auto-fluorescence.

Though, in order to suppress the influence of strain of the fluorescence spectrum due to scatter or the like, the corrected spectrum of auto-fluorescence or the whole intensity of the corrected spectrum of auto-fluorescence is calculated in this embodiment, it is possible as in the conventional to determine the tissue properties on the basis of the uncorrected spectrum of the auto-fluorescence or the whole intensity of the uncorrected spectrum of auto-fluorescence.

Further, in the determination portion 242, it is determined that the object part is diseased when the result of determination based on the fluorescence from the fluorescence agent and the result of determination based on the auto-fluorescence both say that the object part is diseased, that the probability that the object part is diseased is 75% when the result of determination based on the fluorescence from the fluorescence agent says that the object part is diseased and the result of determination based on the auto-fluorescence says that the object part is normal, that the probability that the object part is diseased is 50% when the result of determination based on the fluorescence from the fluorescence agent says that the object part is normal and the result of determination based on the auto-fluorescence say that the object part is diseased, and that the object part is normal when the result of determination based on the fluorescence from the fluorescence agent and the result of determination based on the auto-fluorescence both say that the object part is normal.

Otherwise the determination portion 242 may determine that the object part is normal when the result of determination based on the fluorescence from the fluorescence agent and the result of determination based on the auto-fluorescence both say that the object part is normal and otherwise that the object part is diseased. Or the determination portion 242 may determine that the object part is diseased when the result of determination based on the fluorescence from the fluorescence agent and the result of determination based on the auto-fluorescence both say that the object part is diseased and otherwise that the object part is normal.

As can be understood from the description above, since the system of this embodiment has a spectrum detecting means which detects the spectrum of fluorescence emitted from the object part 1, the fluorescence from the fluorescence agent information and the auto-fluorescence information can be obtained from a desired point. Further, since the tissue properties are determined on the basis of both the result of determination based on the fluorescence from the fluorescence agent and the result of determination based on the auto-fluorescence, a more reliable result of determination can be obtained.

What is claimed is:

1. A fluorescence detecting system comprising:
a stimulating light projecting means which projects onto an object part, which has been dosed with a fluorescence agent, first stimulating light in an exciting wavelength range of the fluorescence agent and second stimulating light which differs from the first stimulating light in the exciting wavelength range and is in an exciting wavelength range of an auto-fluorescence material contained in the object part;
a fluorescence information obtaining means which obtains fluorescence from fluorescence agent information based on fluorescence from the fluorescence agent emitted from the object part in response to the projection of the first stimulating light and the auto-fluorescence information based on auto-fluorescence emitted from the object part in response to the projection of the second stimulating light, wherein the fluorescence agent does not emit fluorescence in response to the projection of the second stimulating light; and
a determining means which determines a tissue property of the object part on the basis of the fluorescence from the fluorescence agent information and the auto-fluorescence information, wherein
the determining means determines:
that the tissue property of the object part is diseased if both a result of the determination based on the fluorescence from the fluorescence agent information and a result of the determination based on the auto-fluorescence information indicate that the object part is diseased,
that the tissue property of the object part is normal if both the result of the determination based on the fluorescence from the fluorescence agent information and the result of determination based on the auto-fluorescence information indicate that the object part is normal, and
that a probability that the tissue property of the object part diseased is greater in a case that the result of the determination based on the fluorescence from the fluorescence agent information indicates that the object part is diseased and the result of the determination based on the auto-fluorescence information indicates that the object part is normal, than in a case that the result of the determination based on the fluorescence from the fluorescence agent information indicates that the object part is normal and the result of the determination based on the auto-fluorescence information indicates that the object part is diseased.

2. A fluorescence detecting system as defined in claim 1 in which the first stimulating light is not shorter than 700 nm and not longer than 800 nm, and the second stimulating light is not shorter than 400 nm and not longer than 430 nm.

3. A fluorescence detecting system as defined in claim 2 further comprising a display means which displays the fluorescence from the fluorescence agent information and auto-fluorescence information at one time.

4. A fluorescence detecting system as defined in claim 2 in which the determining means calculates a determination value by calculating the fluorescence from a value of the fluorescence agent reflecting the tissue property of the object part on the basis of the fluorescence from the fluorescence agent information and a value of the auto-fluorescence reflecting the tissue property of the object part on the basis of the auto-fluorescence information and by calculating the determination value according to one of following formulae:

$$\text{determination value} = \text{auto-fluorescence value} \cdot w1 - \text{fluorescence from the fluorescence agent value} \cdot w2 \quad (1); \text{and}$$

$$\text{determination value} = \text{auto-fluorescence value} \cdot w3 - (1/\text{fluorescence from the fluorescence agent value}) \cdot w4 \quad (2),$$

wherein w1, w2, w3 and w4 are weighting coefficients which have been set in advance.

5. A fluorescence detecting system as defined in claim 2 in which the fluorescence information obtaining means has an image taking means which two-dimensionally images the fluorescence emitted from the object part.

6. A fluorescence detecting system as defined in claim 2 in which the fluorescence information obtaining means has a spectrum detecting means which detects a spectrum of the fluorescence emitted from the object part.

7. A fluorescence detecting system as defined in claim 2 in the form of an endoscope which is inserted into an organic body through a cavity in the organic body.

8. A fluorescence detecting system as defined in claim 1 further comprising a display means which displays the fluorescence from the fluorescence agent information and auto-fluorescence information at one time.

9. A fluorescence detecting system as defined in claim 1 in which the determining means calculates a determination value by calculating the fluorescence from a value of the fluorescence agent reflecting the tissue property of the object part on the basis of the fluorescence from the fluorescence agent information and a value of the auto-fluorescence reflecting the tissue property of the object part on the basis of the auto-fluorescence information and by calculating the determination value according to one of following formulae:

$$\text{determination value} = \text{auto-fluorescence value} \cdot w1 - \text{fluorescence from the fluorescence agent value} \cdot w2 \quad (1); \text{and}$$

$$\text{determination value} = \text{auto-fluorescence value} \cdot w3 - (1/\text{fluorescence from the fluorescence agent value}) \cdot w4 \quad (2),$$

wherein w1, w2, w3 and w4 are weighting coefficients which have been set in advance.

10. A fluorescence detecting system as defined in claim 1 in which the fluorescence information obtaining means has an image taking means which two-dimensionally images the fluorescence emitted from the object part.

11. A fluorescence detecting system as defined in claim 1 in which the fluorescence information obtaining means has a spectrum detecting means which detects a spectrum of the fluorescence emitted from the object part.

12. A fluorescence detecting system as defined in claim 1 in the form of an endoscope which is inserted into an organic body through a cavity in the organic body.

13. A fluorescence detecting system according to claim 1, wherein the fluorescence information obtaining means alternately obtains the fluorescence agent information and the auto-fluorescence information based on an alternate application of the first stimulating light and the second stimulating light.

* * * * *